US008003356B2

(12) United States Patent
Ben-Bassat et al.

(10) Patent No.: US 8,003,356 B2
(45) Date of Patent: Aug. 23, 2011

(54) METHODS FOR THE PREPARATION OF PARA-HYDROXYCINNAMIC ACID AND CINNAMIC ACID AT ALKALINE PH

(75) Inventors: Arie Ben-Bassat, Newark, DE (US); Fateme Sima Sariaslani, Wilmington, DE (US); Lisa L. Huang, Hockessin, DE (US); Ranjan Patnaik, Newark, DE (US); David J. Lowe, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/105,259

(22) Filed: Apr. 13, 2005

(65) Prior Publication Data
US 2005/0260724 A1 Nov. 24, 2005

Related U.S. Application Data

(60) Provisional application No. 60/563,633, filed on Apr. 20, 2004.

(51) Int. Cl.
*C12P 13/22* (2006.01)
*C12P 7/40* (2006.01)
*C12N 1/21* (2006.01)

(52) U.S. Cl. ............... 435/136; 435/252.3; 435/232
(58) Field of Classification Search ............ None
See application file for complete search history.

(56) References Cited

U.S. PATENT DOCUMENTS

| | | | |
|---|---|---|---|
| 5,484,716 A * | 1/1996 | Katsumata et al. | 435/108 |
| 6,368,837 B1 * | 4/2002 | Gatenby et al. | 435/146 |
| 6,521,748 B2 * | 2/2003 | Tang | 536/23.2 |
| 7,378,261 B2 * | 5/2008 | Ben-Bassat et al. | 435/156 |
| 2003/0079255 A1 | 4/2003 | Qi et al. | |
| 2004/0059103 A1 | 3/2004 | Huang et al. | |
| 2004/0229326 A1 | 11/2004 | Ben-Bassat et al. | |
| 2004/0248267 A1 * | 12/2004 | Ben-Bassat et al. | 435/156 |

OTHER PUBLICATIONS

Kim et al. phytochem., 1996, vol. 43 pp. 351-357.*
Kyndt et al. FEBS lett 2002, 512, 240-244.*
Stancik et al. J. Bactrol. 2002, 184, 4246-4258.*
Wookey et al. J. bactrol. 1984, 166, 169-174.*
Crocker et al. Microbiol. 2000, 146, 1295-1310.*
Hitchcock , J. Gen. physiol. 1924, 747-757.*
U.S. Appl. No. 10/138,970, filed May 3, 2002, Qi et al.
U.S. Appl. No. 10/824,237, filed Apr. 14, 2004, Ben-Bassat et al.
Daniel S. Hodgins, Purification, Properties, and the Identification of Catalytically Essential Dehydroalanine, The Journal of Biological Chemistry, vol. 246(9):2977-2985, 1971.
Christopher T. Evans et al., Biotransformation of trans-cinnamic acid to L-phenlalanine: optimization of reaction conditions using whole yeast cells, Enzyme Microb. Technol., vol. 9:417-421, 1987.
Christopher T. Evans et al., Novel stabilization of phenlalanine ammonia-lyase catalyst during bioconversion of trans-cinnamic acid to L-phenylalanine, Appl. Microbiol., Biotechnol., vol. 25:399-405, 1987.
Christopher T. Evans et al, Effect of glycerol, polyethylene glycol and glutaraldehyde on stability of phenylalanine ammonia-lyase activity in yeast, Journal of Industrial Microbiology, vol. 2:53-58, 1987.
Jens Rosler et al., Maize Phenylalanine Ammonia-Lyase Has Tyrosine Ammonia-Lyase Activity, Plant Phys., vol. 113:175-179, 1997.
S. Funfgelder et al., The Activity of Phenylatanine Ammonia-Lyase in Apple Leaves After Wounding, Acta Horticulture, vol. 381:474-478, 1994.
Hye-Won Lim et al., Purification and Properties of Phenylalanine Ammonia-Lyase from Leaf Mustard, Mol. Cells., vol. 7(6):715-720, 1997.
Hye-Won Lim et al., Purification and Properties of Phenylalanine Ammonia-Lyase from Chinese Cabbage, Journal of Biochemistry and Molecular Biology, vol. 31(1):31-36, 1998.
Hye-Won Lim et al., A Second Form of Phenylalanine Ammonia-Lyase from Leaf Mustard, Mol. Cells, vol. 8(3):343-349, 1998.
Annamraju D. Sarma et al., Purification and characterization of UV-B Induced phenylalaine ammonia-lyase from rice seedings, Phytochemistry, vol. 50:729-737, 1999.
A.A. Ameapuymrh et al.. Biotekhnologiya, vol. 2:24-28, 2000.
Jesus Jorrin et al., Purification and properties of phenylalanine ammonia-lyase from sunflower (*Helianthus annus* L.) hypocotyls, Biochimica et Biophysica Acta, vol. 964:73-82, 1988.
Cochrane, Fiona C. et al., The *Arabidopsis* phenylalanine ammonia lyase gene family: kinetic characterization of the four PAL isoforms, Phytochemistry, Jun. 20, 2004, 1557-1564. vol. 65, Elsevier Ltd.
Kim, Seong Hwan et al., Purification and Charcterization of Phenylalanine Ammonia-Lyase From Ustilago Maydis, Phytochemistry, Mar. 18, 1996, 351-357, vol. 43, No. 2, Elsevier Science Ltd., Great Britain.
Gale, E.F. and Epps, H.M.R., The effect of the pH of the medium during growth on the enzymatic activities of bacteria (*Escherichia coli* and *Micrococcus* lysodeikticus) and the biological significances of the changes produced, Biochemical J. (1942) 36(7-9):600-618.
Zilberstein, D. et al., "*Escherichia coli* intracellular pH, membrane potential, and cell growth," J. Bacteriol. (1984) 158 (1):246-252.

* cited by examiner

*Primary Examiner* — Tekchand Saidha
*Assistant Examiner* — Younus Meah

(57) ABSTRACT

Methods for the microbial production of para-hydroxycinnamic acid (pHCA) and cinnamic acid (CA) are provided. Microbes producing either tyrosine or phenylalanine are grown in the presence of either tyrosine ammonium lyase or phenylalanine ammonium lyase respectively where some part of the fermentation is accomplished at alkaline pH. The process results in greater yields and higher rates of para-hydroxycinnamic acid (pHCA) and cinnamic acid (CA) production as compared with fermentation exclusively at physiological pH.

7 Claims, 2 Drawing Sheets

METHODS FOR THE PREPARATION OF PARA-HYDROXYCINNAMIC ACID AND CINNAMIC ACID AT ALKALINE PH

This application claims the benefit of U.S. Provisional Application 60/563,633, filed Apr. 20, 2004.

FIELD OF THE INVENTION

The invention relates to the field of industrial microbiology. More specifically, methods for the enhancement of yield and rate of production of aromatic carboxylic acids such as para-hydroxycinnamic acid and cinnamic acid are disclosed.

BACKGROUND OF THE INVENTION

Para-hydroxycinnamic acid (pHCA) and cinnamic acid (CA) are multifunctional aromatic compounds that have potential utility in a wide variety of industrial applications. For example, these aromatic compounds have application as monomers for the production of liquid crystalline polymers, and in the production of resins, elastomers, coatings, adhesives, automotive finishes and inks.

Chemical synthetic methods for producing these aromatic compounds are known. However, these chemical methods are expensive due to the high cost of the starting materials and the extensive product purification required. Moreover, these methods generate large amounts of unwanted byproducts. Consequently, biological production methods for these aromatic compounds have been developed. For example, Gatenby et al. in U.S. Pat. No. 6,368,837 describe several methods for producing pHCA from glucose using bioengineered microorganisms. Additionally, Qi et al. in copending and commonly owner U.S. patent application Ser. No. 10/138,970 and U.S. Patent Application Publication No. 2003/007925 describe methods for producing CA and pHCA using recombinant microorganisms comprising at least one gene encoding a tyrosine ammonium lyase (TAL) activity and at least one gene encoding a phenylalanine hydroxylase (PAH) activity. However, a problem encountered with the biological production of these aromatic compounds is endproduct inhibition, which limits product yield. Additionally, the fermentation is typically run at a pH that is not optimal for the tyrosine ammonium lyase activity, required to convert tyrosine to pHCA, or the phenylalanine ammonia lyase (PAL) activity, required to convert phenylalanine to CA. The pH optimum for these enzymes is in the alkaline pH range, typically about pH 8.5 (see for example Hodgins, *J. Biol. Chem.* 246:2977-2985 (1971)).

Evans et al. (*Enzyme and Microbial Technology* 9:417-421 (1987); *Appl. Microbiol. Biotechnol.* 25:399-405 (1987); and *Journal of Industrial Microbiology.* 2:53-58 (1987)) describe methods for the biotransformation of trans-cinnamic acid to phenylalanine using whole yeast cells, which have phenylalanine ammonia lyase activity, at a pH of 9.0 to 12.0. However, those disclosures do not describe the bioproduction of pHCA or CA in a two stage fermentation in which the pH is raised to alkaline values during the second stage of the fermentation.

One approach to mitigate end-product inhibition is to use two-phase extractive fermentation, in which the pHCA or CA produced by a recombinant production host is extracted into an immiscible organic phase during the fermentation so that it never reaches an inhibitory or critical concentration, as described by Ben Bassat et al. in copending and commonly owned U.S. patent application Ser. No. 10/824,237. The methods described in that disclosure resulted in improved yields for pHCA and CA. However, still higher yields are required for commercial applications.

Therefore, the need exists for a method for producing para-hydroxycinnamic acid and cinnamic acid in high yield for commercial applications.

Applicants have solved the stated problem by discovering methods for producing para-hydroxycinnamic acid and cinnamic acid in high yield using two-stage fermentation, wherein the pH is increased to alkaline values during the second stage of the fermentation.

SUMMARY OF THE INVENTION

The invention provides methods for the enhanced production of aromatic carboxylic acids such as pHCA and CA by fermentation under the influence of a tyrosine ammonia lyase or phenylalanine ammonia lyase enzyme where the catalytic event takes place at alkaline pH.

Accordingly the invention provides a method for the production of para-hydroxycinnamic acid comprising:
(i) providing a microbial production host cell which
   a) makes tyrosine when grown with a fermentable carbon substrate; and
   b) comprises a gene encoding a polypeptide having tyrosine ammonia lyase activity operably linked to suitable regulatory sequences;
(ii) contacting the host cell of (i) with a fermentable carbon substrate in a growth medium at physiological pH for a time sufficient to allow tyrosine to accumulate in the growth medium; and
(iii) raising the pH of the growth medium to a pH of about 8.0 to about 11.0 for a time sufficient to allow para-hydroxycinnamic acid to accumulate; and
(iv) optionally recovering said para-hydroxycinnamic acid.

In a related embodiment the invention provides a method for the production of cinnamic acid comprising:
(i) providing a microbial production host cell which
   a) makes phenylalanine when grown with a fermentable carbon substrate;
   b) comprises a gene encoding a polypeptide having phenylalanine ammonia lyase activity operably linked to suitable regulatory sequences;
(ii) contacting the host cell of (i) with a fermentable carbon substrate in a growth medium at physiological pH for a time sufficient to allow phenylalanine to accumulate in the growth medium; and
(iii) raising the pH of the growth medium to a pH of about 8.0 to about 11.0 for a time sufficient to allow cinnamic acid to accumulate; and
(iv) optionally recovering said cinnamic acid.

Similarly the invention provides a method for the production of para-hydroxycinnamic acid comprising the sequential steps of:
(i) providing a microbial production host cell which makes tyrosine when grown with a fermentable carbon substrate;
(ii) contacting the production host cell of (i) with a fermentable carbon substrate in a growth medium at physiological pH for a time sufficient to allow tyrosine to accumulate in the growth medium;
(iii) contacting the growth medium of (ii) with tyrosine ammonia lyase;
(iv) raising the pH of the growth medium to a pH of about 8.0 to about 11.0 for a time sufficient to allow para-hydroxycinnamic acid to accumulate in the growth medium; and (iv) optionally recovering said para-hydroxycinnamic acid.

In another embodiment the invention provides a method for the production of cinnamic acid comprising the sequential steps of:
(i) providing a microbial production host cell which makes phenylalanine when grown with a fermentable carbon substrate;
(ii) contacting the production host cell of (i) with a fermentable carbon substrate in a growth medium at physiological pH for a time sufficient to allow phenylalanine to accumulate in the growth medium;
(iii) contacting the growth medium of (ii) with phenylalanine ammonia lyase;
(iv) raising the pH of the growth medium to a pH of about 8.0 to about 11.0 for a time sufficient to allow cinnamic acid to accumulate in the growth medium; and
(iv) optionally recovering said cinnamic acid.

Alternatively the invention provides a method for the production of para-hydroxycinnamic acid comprising the sequential steps of:
(i) providing a microbial production host cell which makes tyrosine when grown with a fermentable carbon substrate;
(ii) contacting the production host cell of (i) with a fermentable carbon substrate in a growth medium at physiological pH for a time sufficient to allow tyrosine to accumulate in the growth medium;
(iii) isolating the tyrosine produced in (ii) from the growth medium;
(iv) contacting the isolated tyrosine of (iii) with a source of tyrosine ammonia lyase in a solution having a pH of about 8.0 to about 11.0 for a time sufficient to allow para-hydroxycinnamic acid to accumulate; and
(v) optionally recovering said para-hydroxycinnamic acid.

In similar fashion the invention provides a method for the production of cinnamic acid comprising the sequential steps of:
(i) providing a microbial production host cell which makes phenylalanine when grown with a fermentable carbon substrate;
(ii) contacting the production host cell of (i) with a fermentable carbon substrate in a growth medium at physiological pH for a time sufficient to allow phenylalanine to accumulate in the growth medium;
(iii) isolating the phenylalanine produced in (ii) from the growth medium;
(iv) contacting the isolated phenylalanine of (iii) with a source of phenylalanine ammonia lyase in a solution having a pH of about 8.0 to about 11.0 for a time sufficient to allow cinnamic acid to accumulate in the growth medium; and
(iv) optionally recovering said cinnamic acid.

In another embodiment the invention provides a method for the production of para-hydroxycinnamic acid comprising the sequential steps of:
(i) providing a microbial production host expressing a gene encoding a polypeptide having tyrosine ammonium lyase activity; and
(ii) contacting said microbial production host of (i) with tyrosine at a pH of about 8.0 to about 11.0 wherein para-hydroxycinnamic acid is produced.

In an alternate embodiment the invention provides a method for the production of cinnamic acid comprising the sequential steps of:
(i) providing a microbial production host expressing a gene encoding a polypeptide having phenylalanine ammonium lyase activity; and
(ii) contacting said microbial production host of (i) with phenylalanine at a pH of about 8.0 to about 11.0 wherein cinnamic acid is produced.

BRIEF DESCRIPTION OF THE FIGURES AND SEQUENCE DESCRIPTIONS

The invention can be more fully understood from the following detailed description, figure and the accompanying sequence descriptions, which form a part of this application.

Figure 1:
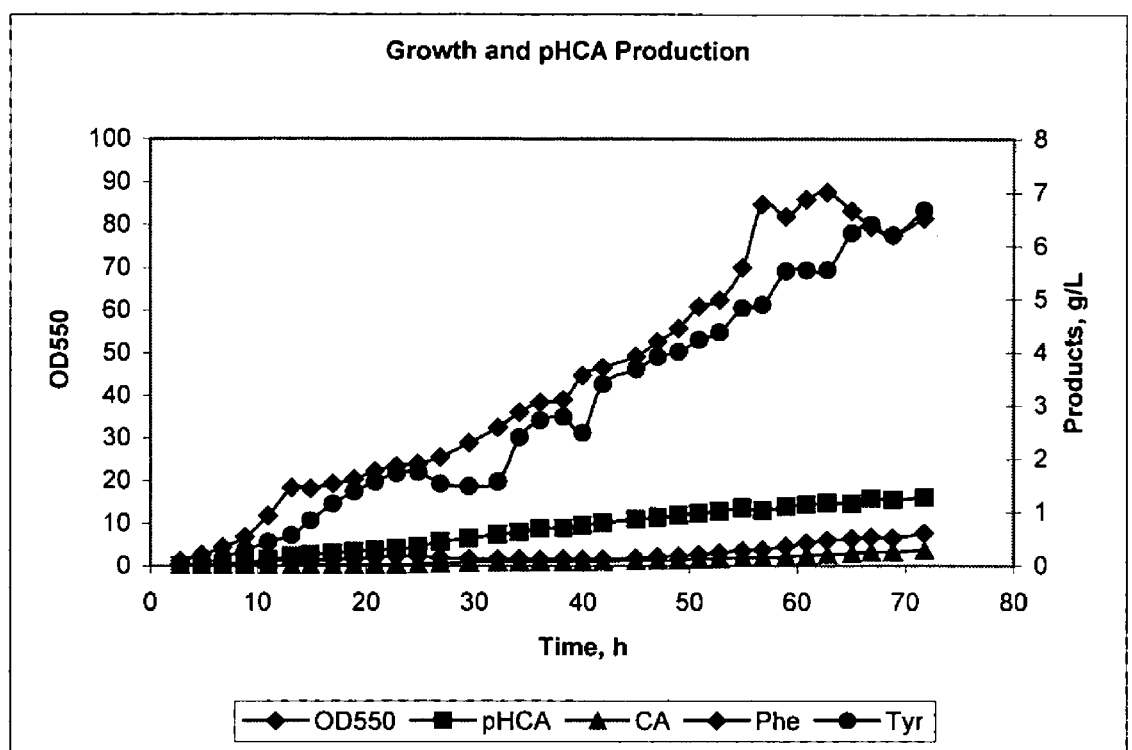
FIG. 1 shows the growth and pHCA production in a fermentation with no pH change.

The following sequences conform with 37 C.F.R. 1.821-1.825 ("Requirements for Patent Applications Containing Nucleotide Sequences and/or Amino Acid Sequence Disclosures—the Sequence Rules") and consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NO:1 is the nucleotide sequence of the gene encoding the phenylalanine-tyrosine ammonia lyase (PAL/TAL) enzyme from *Rhodotorula glutinis*.

SEQ ID NO:2 is the amino acid sequence of the phenylalanine-tyrosine ammonia lyase (PAL/TAL) enzyme from *Rhodotorula glutinis*.

SEQ ID NOs:3-6 are the nucleotide sequences of primers used to construct *E. coli* strain DPD4009.

SEQ ID NOs:7 and 8 are the nucleotide sequences of primers used to confirm the successful construction of *E. coli* strain WS158.

SEQ ID NOs:9 and 10 are the nucleotide sequences of primers used to amplify the pal gene from *Rhodotorula glutinis*.

SEQ ID NOs:11 and 12 are the nucleotide sequences of primers used to construct plasmid pLH276.

DETAILED DESCRIPTION OF THE INVENTION

The invention relates to methods for improving the yield and rate of production of para-hydroxycinnamic acid (pHCA) and cinnamic acid (CA). Microbes having the ability to produce either tyrosine or phenylalanine are grown in the presence of enzymes having tyrosine ammonium lyase (TAL) activity or phenylalanine ammonium lyase (PAL) activity for the production of para-hydroxycinnamic acid (pHCA) and cinnamic acid (CA), respectively. Production yields and rates of the aromatic carboxylic acid product is enhanced at pH's of about 8.0 to about 11.0.

The production of para-hydroxycinnamic and cinnamic acid are useful as monomers in a number of industrial applications including the production of resins, elastomers, coatings, adhesives, automotive finishes and inks. For example para-hydroxycinnamic acid (pHCA) and cinnamic acid (CA) may be used as a monomers for the production of Liquid Crystal Polymers (LCP). LCPs are polymers that exhibit an intermediate or mesophase between the glass-transition temperature and the transition temperature to the isotropic liquid or have at least one mesophase for certain ranges of concentration and temperature. The molecules in these mesophases behave like liquids and flow, but also exhibit the anisotropic properties of crystals. LCPs are used in liquid crystal displays, and in high speed connectors and flexible circuits for electronic, telecommunication, and aerospace applications. Because of their resistance to sterilizing radiation and their high oxygen and water vapor barrier properties, LCPs are used in medical devices, and in chemical and food packaging.

The following abbreviations and definitions should be used for the interpretation of the specification and the claims.

"Phenylalanine ammonia-lyase" is abbreviated PAL.

"Tyrosine ammonia-lyase" is abbreviated TAL.

"Para-hydroxycinnamic acid" is abbreviated pHCA.

As used herein the terms "cinnamic acid" and "cinnamate" are used interchangeably and are abbreviated CA.

The term "TAL activity" refers to the ability of a protein to catalyze the direct conversion of tyrosine to pHCA.

The term "PAL activity" refers to the ability of a protein to catalyze the conversion of phenylalanine to cinnamic acid.

"pal" represents a gene that encodes an enzyme with PAL activity.

"tal" represents a gene that encodes an enzyme with TAL activity.

The term "PAL/TAL activity" or "PAL/TAL enzyme" refers to a protein which contains both PAL and TAL activity. Such a protein has at least some specificity for both tyrosine and phenylalanine as an enzymatic substrate.

As used herein the terms "protein" and "polypeptide" will be used interchangeably.

"Gene" refers to a nucleic acid fragment that expresses a specific protein, including regulatory sequences preceding (5' non-coding sequences) and following (3' non-coding sequences) the coding sequence. "Native gene" or "wild type gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes.

"Transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

The terms "plasmid", "vector" and "cassette" refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

"Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". Promoters which are only turned on in response to an inducing stimulus are referred to as "inducible promoters". The inducing stimulus may include a variety of agents including chemicals, the presence of common metabolic end products as well as physical stimuli such as heat. It is further recognized that since in most cases the exact boundaries of regulatory sequences have not been completely defined, DNA fragments of different lengths may have identical promoter activity.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression" as used herein is intended to mean the transcription and translation to gene product from a gene coding for the sequence of the gene product. In the expression, a DNA chain coding for the sequence of gene product is first transcribed to a complementary RNA which is often a messenger RNA and, then, the thus transcribed messenger RNA is translated into the above-mentioned gene product if the gene product is a protein.

The term "fermentable carbon substrate" refers to a carbon source capable of being metabolized by host organisms of the present invention and particularly carbon sources selected from the group consisting of monosaccharides, oligosaccharides, polysaccharides, carbon dioxide, methanol, formaldehyde, formate, and carbon-containing amines. and/or mixtures thereof.

The term "production host" refers to a microorganism having the ability to produce tyrosine or phenylalanine at high levels (over-producer). Additionally, production hosts of the invention may comprise genes encoding enzymes having either TAL or PAL activity.

"Over-producing strain" refers to a recombinant microorganism that produces a gene product at a level that exceeds the level of production in normal or non-transformed microorganisms. The term over-producing strain as used herein will typically refer to those microbial strains that over-produce either tyrosine or phenylalanine.

As used herein the term "accumulate" when applied to an aromatic amino acid means that the aromatic acid concentration within the growth medium increases over time.

As used herein the term "rate" means amount of product made per unit time, wherein the amount of product will be expressed as a concentration i.e. g/L, or mM, for example.

The term "yield" may be defined as the final titer of product, or final concentration of product at the end of a fermentation run.

The term "physiological pH" or "physiological conditions" refers to the pH range at which the production host retains good growth and active metabolism. Although most bacterial production hosts operate optimally at a pH of about 6.5 to about 7.5, there are those that operate optimally outside that range and their "physiological pH" would correspond to those subjective conditions. For example, many yeast operate at relatively low pH such as 3.5 to about 7.5, which would represent "physiological conditions" for these organisms.

As used herein the term "alkaline pH" means a pH equal to or above 8.0.

Standard recombinant DNA and molecular cloning techniques used here are well known in the art and are described by Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory Cold Press Spring Harbor, N.Y. (1984); and by Ausubel, F. M. et al., *Current Protocols in Molecular Biology*, published by Greene Publishing Assoc. and Wiley-Interscience (1987).

The invention relates to a method for the production of pHCA or CA in a fermentation process. The production of cinnamic acid follows from the contacting of phenylalanine with an enzyme having PAL activity.

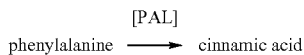

The production of pHCA follows from the contacting of tyrosine with an enzyme having TAL activity.

Typically the process of the invention proceeds in two stages. In one embodiment the first stage comprises providing a microbial production host having an enhanced ability to produce the aromatic amino acids tyrosine or phenylalanine (an over-producer). These cells are grown at physiological pH to a point where the amino acid is accumulated in the growth medium. At this point it may be optimal to isolate the tyrosine or phenylalanine from the growth media before further processing, however it is not necessary to do so. During the second stage of the fermentation the cells are contacted with a source of either TAL (in the case of the tyrosine producing cells or PAL (in the case of phenylalanine producing cells) at a pH of about 8.0 to about 11.0. During this stage the amino acid is converted to the corresponding aromatic carboxylic acid at relatively high rates and yields.

In an alternate embodiment, the process again comprises two stages; however, the microbial production host is now provided with the ability to produce the aromatic carboxylic acid. Here, the overproducing production host will additionally have the ability to express either TAL or PAL. In the first stage cells are grown at physiological pH to accumulate aromatic amino acid and in the second stage, the pH is increased to about 8.0 to about 11.0 to maximize the conversion of aromatic amino acid substrate to the corresponding aromatic carboxylic acid product.

Sources of TAL and PAL

The present invention makes use of the enzymes having either tyrosine ammonium lyase (TAL) activity or phenylalanine ammonium lyase (PAL) activity. Enzymes having these activities are ubiquitous and easily obtained by the person of skill in the art.

Phenylalanine Ammonium Lyase (PAL), and Tyrosine Ammonium Lyase (TAL)

Genes encoding PAL are known in the art and several have been sequenced from both plant and microbial sources (see for example EP 321488 *[R. toruloides]*; WO 9811205 *[Eucalyptus grandis* and *Pinus radiata]*; WO 9732023 [Petunia]; JP 05153978 *[Pisum sativum]*; WO 9307279 [potato, rice]). The sequence of PAL genes is available (see for example GenBank AJ010143 and X75967). The gene encoding the PAL enzyme from *Rhodotorula glutinis* is given as SEQ ID NO:1. Where expression of a wild type PAL gene in a recombinant host is desired, the wild type gene may be obtained from any source including but not limited to, yeasts such as *Rhodotorula* sp., *Rhodosporidium* sp. and *Sporobolomyces* sp.; bacterial organisms such as *Streptomyces*; and plants such as pea, potato, rice, eucalyptus, pine, corn, petunia, *arabidopsis*, tobacco, and parsley. Within the context of the present invention genes isolated from the organisms *Rhodotorula* sp., *Rhodosporidium* sp., *Rhodotorula glutinis*, and *Sporobolomyces* sp. are preferred.

There are no known genes which encode an enzyme having exclusively TAL activity, i.e., which will use only tyrosine as a substrate for the production of pHCA. Several of the PAL enzymes mentioned above have some substrate affinity for tyrosine. Thus, genes encoding TAL activity may be identified and isolated concurrently with the PAL genes described above. For example, the PAL enzyme isolated from parsley (Appert et al., *Eur. J. Biochem.* 225:491 (1994)) and corn ((Havir et al., *Plant Physiol.* 48:130 (1971)) both demonstrate the ability to use tyrosine as a substrate. Similarly, the PAL enzyme isolated from *Rhodotorula glutinis*, (Hodgins D S, *J. Biol. Chem.* 246:2977 (1971)), given as SEQ ID NO:2, also may use tyrosine as a substrate. Such enzymes will be referred to herein as PAL/TAL enzymes or activities. Where it is desired to create a recombinant organism expressing a wild type gene encoding PAL/TAL activity, genes isolated from maize, wheat, parsley, *Rhizoctonia solani*, *Rhodosporidium*, *Sporobolomyces pararoseus* and *Rhodosporidium* may be used as discussed in Hanson and Havir, *The Biochemistry of Plants*; Academic: New York, 1981; Vol. 7, pp 577-625, where the genes isolated from *Rhodosporidium* sp. *Rhodotorula glutinis*, *Trichosporon cutaneum*, *Rhodobacter sphaeroides*, and *Rhodobacter capsulatus* are preferred.

Methods of obtaining these or homologous wild type genes using sequence-dependent protocols are well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction (PCR), ligase chain reaction (LCR)).

For example, genes encoding homologs for anyone of the mentioned activities (PAL, or TAL) could be isolated directly by using all or a portion of the known sequences as DNA hybridization probes to screen libraries from any desired plant, fungi, yeast, or bacteria using methodology well known to those skilled in the art. Specific oligonucleotide probes based upon the literature nucleic acid sequences can be designed and synthesized by methods known in the art (Maniatis, supra). Moreover, the entire sequences can be used directly to synthesize DNA probes by methods known to the skilled artisan such as random primers DNA labeling, nick translation, or end-labeling techniques, or RNA probes using available in vitro transcription systems. In addition, specific primers can be designed and used to amplify a part of or full-length of the instant sequences. The resulting amplification products can be labeled directly during amplification reactions or labeled after amplification reactions, and used as probes to isolate full length cDNA or genomic fragments under conditions of appropriate stringency.

In addition, two short segments of the literature sequences may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the literature sequences, and the sequence of the other primer takes advantage of the presence of the polyadenylic acid tracts to the 3' end of the mRNA precursor encoding bacterial genes. Alternatively, the second primer sequence may be based upon sequences derived from the cloning vector. For example, the skilled artisan can follow the RACE protocol (Frohman et al., *PNAS USA* 85:8998 (1988)) to generate cDNAs by using PCR to amplify copies of the region between a single point in the transcript and the 3' or 5' end. Primers oriented in the 3' and 5' directions can be designed from the literature sequences. Using commercially available 3' RACE or 5' RACE systems (Invitrogen, Carlsbad, Calif.), specific 3' or 5' cDNA fragments can be isolated (Ohara et al., *PNAS USA* 86:5673 (1989); Loh et al., *Science* 243:217 (1989)).

In one embodiment the TAL or PAL enzymes may used in the present invention as being expressed in the microbial production host or in some other microbial cell. Methods for the transformation of host cells with the appropriate genes are discussed below. Alternatively, partially purified or purified enzyme may be added to the fermentation culture at a point where the pH is in the alkaline range, thereby effecting the production of the desired aromatic carboxylic acid product.

Methods for obtaining purified or partially purified enzyme are common and well known. For example, TAL or PAL may be isolated from microbial cells in the following manner. The cells are separated from the culture medium using known methods including, but not limited to centrifugation or filtration. The cells are washed and then disrupted using a French press, an ultrasonic disrupter, a homogenizer, a Dyno Mill, or other means known in the art, to obtain a cell-free extract. The cell-free extract is centrifuged to remove cell debris. In one embodiment, the cell-free extract is used as the source of enzyme activity.

Optionally the TAL or PAL enzyme is purified from the cell-free extract using methods known in the art, including but not limited to ammonium sulfate precipitation, anion exchange chromatography, hydrophobic interaction chromatography, size exclusion chromatography, electrophoresis and the like. When the TAL or PAL enzyme is produced extracellularly the culture medium may be treated in the same manner as described for the cell-free extract to obtain the purified enzyme.

Alternatively the enzyme may be immobilized prior to use. Methods of cell and enzyme immobilization are well-know in the art (see for example, Weetal, *Methods in Enzymology*, Vol. XLIV, K. Mosbach, ed., Academic Press, New York (1976), Bickerstaff, *Immobilization of Enzymes and Cells*, Methods in Biotechnology Series, Humana Press, Totowa, N.J. (1997), and Taylor, *Protein Immobilization: Fundamentals and Applications*, BioProcess Technology, vol. 14, Marcel Dekker, New York (1991)). For example, the enzyme source having TAL or PAL activity may be immobilized by entrapment in a polymer gel, adsorption onto a solid support, covalent crosslinking using a bifunctional reagent, or covalent binding to an insoluble matrix, such as glass, polystyrene, nylon, or polyacrylic acid derivatives. In one embodiment, a cell-free extract or the purified enzyme is immobilized by covalent attachment to oxirane acrylic beads, available from Sigma Chemical (St. Louis, Mo.). In another embodiment, wildtype or recombinant host cells are immobilized by entrapment in calcium alginate beads, as described by Bickerstaff, supra. Optionally, the entrapped cells may be cross-linked by polyethyleneimine and glutaradehyde or other suitable crosslinking agents known in the art.

Microbial Production Hosts

The invention provides microbial production hosts which have the ability to produce the aromatic amino acids, tyrosine and phenylalanine. A number of microbial host cells are suitable for this purpose including, but are not limited to *Escherichia, Methylosinus, Methylomonas, Pseudomonas, Streptomyces, Corynebacterium*, and *Rhodobacter*. The preferred host cells of the instant invention are *Escherichia coli* and *Pseudomonas putida*.

The most preferred host cells of the instant invention are mutant strains of these bacteria that overproduce either phenylalanine or tyrosine. Tyrosine overproducing strains are preferred for the production of pHCA using an enzyme having TAL activity. Alternatively, phenylalanine overproducing strains are preferred for the production of CA using an enzyme having PAL activity.

Tyrosine overproducing strains are known and include, but are not limited to *Corynebacteria, Brevibacteria, Microbacterium, E. coli, Arthrobacter, Candida, Citrobacter, Pseudomonas* and *Methylomonas*. Particularly useful tyrosine overproducing strains include but are not limited to *Microbacterium ammoniaphilum* ATCC 10155, *Corynebactrium lillium* NRRL-B-2243, *Brevibacterium divaricatum* NRRL-B-2311, *Arthrobacter citreus* ATCC 11624, and *Methylomonas* SD-20. Other suitable tyrosine over-producers are known in the art, see for example *Microbial production of L-tyrosine: A Review*, T. K. Maiti et al, Hindustan Antibiotic Bulletin, vol 37, 51-65, 1995. Additionally an example of an *Escherichia* tyrosine overproducing strain that may be used is *E. coli* TY1, available from OmniGene Bioproducts, Inc. Cambridge, Mass.

Phenylalanine overproducing strains are known and include but are not limited to *E. coli, Microbacterium Corynebacteria, Arthrobacter, Pseudomonas* and *Brevibacteria*. Particularly useful phenylalanine overproducing strains include, but are not limited to *Microbacterium ammoniaphilum* ATCC 10155, *Corynebactrium lillium* NRRL-B-2243, *Brevibacterium divaricatum* NRRL-B-2311, *E. coli* NST74 and *Arthrobacter citreus* ATCC 11624. Other suitable phenylalanine overproducing strains are known and a review may be found in Maiti et al, supra and *Metabolic Engineering For Microbial Production Of Aromatic Amino Acids And Derived Compounds*, J. Bongaertes et al., *Metabolic Engineering* vol 3, 289-300, 2001. Additionally an example of a phenylalanine overproducing strain that may be used is *E. coli* NST74, available as strain ATCC No. 31884 from the American Type Culture Collection, Manassas, Va.

In one embodiment the production host may additionally contain genes that encode enzymes having TAL or PAL activity. In an alternate embodiment the TAL and PAL enzymes may be expressed in a host that is not the production host but is simply suitable for the expression of these enzymes. In either case methods of introducing the genes into the appropriate host cell using appropriate vectors and transformation techniques are well known and protocols are commonly available (see Maniatis, supra).

Vectors or cassettes useful for the transformation of suitable host cells are well known in the art. Typically the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host.

Initiation control regions or promoters which are useful to drive expression of the instant TAL or PAL gene in the desired host cell are numerous and familiar to those skilled in the art. Virtually any promoter capable of driving these genes is suitable for the present invention including, but not limited to: CYC1, HIS3, GAL1, GAL10, ADH1, PGK, PHO5, GAPDH, ADC1, TRP1, URA3, LEU2, ENO, TPI (useful for expression in *Saccharomyces*); AOX1 (useful for expression in *Pichia*); and lac, ara, tet, trp, $IP_L$, $IP_R$, T7, tac, and trc (useful for expression in *Escherichia coli*) as well as the amy, apr, npr promoters and various phage promoters useful for expression in *Bacillus*.

Termination control regions may also be derived from various genes native to the preferred hosts. Optionally, a termination site may be unnecessary; however, it is most preferred if included.

In one embodiment it may be useful to engineer an overproducing strain to contain either a TAL or PAL gene under the control of an inducible promoter. In such an embodiment cells would be grown at physiological pH for a time sufficient to accumulate the aromatic amino acid in the growth medium. Subsequently, an inducer could be added to the culture that would stimulate the expression of the TAL or PAL gene concurrently with the raising of the pH to the alkaline range. In this manner a single cell could serve as the source of both the aromatic amino acid as well as the enzyme. Inducible promoters are common and well known in the art (see Maniatis, supra)

Once the vectors are constructed, host cells may be transformed by the common techniques of electroporation or conjugal mating (see Maniatis, Supra)

Fermentation Conditions

Once the desired production host has been constructed or selected it may be used in the present two stage method for the high level production of pHCA or CA. In one preferred embodiment a production host having the ability to overproduce tyrosine or phenylalanine is grown at physiological pH (typically, about 6.5 to about 7.5) for a time sufficient to allow the accumulation of the aromatic amino acid. Typically cells in this stage are grown to stationary phase. Following aromatic amino acid accumulation, the culture is contacted with a source of enzyme having either TAL or PAL activity depending on the nature of the aromatic amino acid produced by the host cell. During this second stage of the fermentation the pH of the system is raised to a pH of about 8.0 to about 11.0, where a pH of about 9.5 to about 10.5 is preferred. Typically under these conditions the production host is no longer viable, however the rate and yield of production of the aromatic carboxylic acid product are enhanced at this pH. About a four-fold improvement in yield has been seen over single stage cultures where the pH was maintained at physiological conditions.

In an alternate embodiment the present invention may be practiced in two stages where, in the first stage the production host comprises the genes encoding enzymes having either TAL of PAL activity. In this embodiment the production host will not only have the ability to over-produce the appropriate aromatic amino acid but will also be equipped with the enzyme suitable for its conversion to the desired aromatic carboxylic product. Thus, a tyrosine over-producing host will be transformed with a gene encoding an enzyme having TAL activity and a phenylalanine host will be transformed with a gene encoding an enzyme having PAL activity. Production hosts are grown under physiology conditions (pH of about 6.5 to about 7.5, for industrially useful bacteria and for yeasts about 3.5 to about 7.5) in the first stage. In the second stage the pH is raised to about 8.0 to about 11.0 to effect the enhanced rate and yield of production of pHCA or CA.

In one preferred embodiment it may be useful to control the levels of ammonia in the fermentation culture. For example, the presence of ammonia in the culture may have an inhibitory effect on the rates and yield of the TAL or PAL catalyzed reaction. Hence, removal of ammonia, preferably as it is formed in the fermentation, may enhance the rates and yields of this reaction. Removal of ammonia may be accomplished by means well known in the art. For example aeration or the addition of specific sorbents, such as the mineral clinoptilolite or ion exchange resins are typically suitable means.

For large scale commercial production it is expected fermentations will take place in a fermentor. Any suitable fermentor may be used including a stirred tank fermentor, an airlift fermentor, a bubble fermentor, or any combination thereof. Materials and methods for the maintenance and growth of microbial cultures are well known to those in the art of microbiology or fermentation science (See for example, Bailey et al., *Biochemical Engineering Fundamentals*, second edition, McGraw Hill, New York, 1986).

Consideration must be given to appropriate growth medium, pH, temperature, and requirements for aerobic, microaerobic, or anaerobic conditions, depending on the specific requirements of the microorganism for the specific gene expression. The growth medium used is not critical, but it must support growth of the microorganism used and promote the enzymatic pathway necessary to produce the desired product. A conventional growth medium may be used, including, but not limited to complex media, containing organic nitrogen sources such as yeast extract or peptone and a fermentable carbon source; minimal media and defined media.

Suitable fermentable carbon sources include, but are not limited to monosaccharides, such as glucose or fructose; disaccharides, such as lactose or sucrose; oligosaccharides and polysaccharides, such as starch or cellulose; one-carbon substrates such as carbon dioxide, methanol, formaldehyde, formate, and carbon-containing amines and/or mixtures thereof. In addition to the appropriate carbon source, the growth medium must contain a suitable nitrogen source, such as an ammonium salt, yeast extract or peptone; minerals, salts, cofactors, buffers and other components, known to those skilled in the art (Bailey et al. supra).

Recovery of pHCA and CA

Methods for the recovery of pHCA or CA from a growth medium are available. One preferred method is taught in the copending and commonly owned U.S. patent application Ser.

No. 10/824,237, hereby incorporated by reference. Briefly the method involves first acidifying the fermentation broth containing either the pHCA or CA to a pH or about 4.0 or below and then adding an extractant. Extractants useful for this purpose are water immiscible organic solvents and may includem but are not limited to, diisopentyl ether, n-propyl benzoate, 2-undecanone, dibenzyl ether, 2-tridecanone, 2-decanone, 1-pentanone 1-phenyl, methyl decanoate, 1-undecanol, diisobutyl DBE-IB and mixtures thereof. The pHCA or CA is dissolved in the extractant and removed from the medium. The pHCA or CA may then be recovered from the extractant by well known means such as distillation, adsorption by resins, or separation by molecular sieves. Alternatively, the pHCA or CA may be recovered by acidification of the growth medium to a pH below 2.0, followed by crystallization.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

The meaning of abbreviations used is as follows: "min" means minute(s), "h" means hour(s), "sec" means second(s), "rpm" means revolutions per minute, "µL" means microliter(s), "mL" means milliliter(s), "L" means liter(s), "nm" means nanometer(s), "mm" means millimeter(s), "cm" means centimeter(s), "µm" means micrometer(s), "mM" means millimolar, "M" means molar, "mmol" means millimole(s), "µmol" means micromole(s), "g" means gram(s), "µg" means microgram(s), "mg" means milligram(s), "PCR" means polymerase chain reaction, "OD" means optical density, "$OD_{550}$" means the optical density measured at a wavelength of 550 nm, "$OD_{600}$" means the optical density measured at a wavelength of 600 nm, "HPLC" means high performance liquid chromatography, "IPTG" means isopropyl β-D-thiogalactopyranoside, "kV" means kilovolt(s), "µF" means microfarad(s), "bp" means base pairs, "kPa" means kilopascal(s), "SLPM" means standard liter per minute, "Ferm. wt." means the weight of the liquid fermentation broth, "% w/w" means percent by weight, and "% w/v" means weight/volume percent.

General Methods:

Materials and methods suitable for the maintenance and growth of bacterial cultures are well known in the art. Techniques suitable for use in the following Examples may be found as set out in *Manual of Methods for General Bacteriology*, Phillipp Gerhardt, R. G. E. Murray, Ralph N. Costilow, Eugene W. Nester, Willis A. Wood, Noel R. Krieg and G. Briggs Phillips, eds., American Society for Microbiology, Washington, D.C. (1994) or by Thomas D. Brock in *Biotechnology: A Textbook of Industrial Microbiology*, Second Edition, Sinauer Associates, Inc., Sunderland, Mass. (1989). All chemicals were reagent-grade and were obtained from Sigma Chemical Company (St. Louis, Mich.) or a similar vendor, unless otherwise noted. Yeast extract was obtained from Marcor Development Corp. (Carlstadt, N.J.). Mazu DF204 Defoamer was obtained from BASF Corp. (Mt. Olive, N.J.).

The LB culture medium used in the Examples contains the following per liter of medium: Bacto-tryptone (10 g), Bacto-yeast extract (5 g), and NaCl (10 g).

Construction of Recombinant Bacterial Strains:

The recombinant bacterial strains used in the Examples were constructed using standard recombinant DNA and molecular cloning techniques that are well known in the art and are described in Maniatis, supra; Silhavy, T. J., Bennan, M. L. and Enquist, L. W., supra; and in Ausubel, F. M. et al., supra.

Construction of *E. coli* Strain DPD4009:

*E. coli* strain DPD4009 is a tyrosine-overproducing, plasmid-less, phenylalanine auxotroph, which was derived in several steps from *E. coli* TY1 (DGL430), a tyrosine overproducing strain obtained from OmniGene Bioproducts, Inc. (Cambridge, Mass.). First, TY1 was cured of the plasmid it was carrying to yield a tetracycline-sensitive strain called TS5. Subsequently, TS5 was the recipient in a P1-mediated transduction using *E. coli* strain CAG12158, which carries pheA18::Tn10 (Coli Genetics Stock Center, Yale University, #7421), as the donor. One tetracycline-resistant transductant was called BNT565.2.

*E. coli* strain WS158 was constructed using the two PCR fragments integration method described by Suh in copending and commonly owned U.S. patent application Ser. No. 10/734,936, incorporated herein by reference, via λ-Red recombinase system. A first linear DNA fragment (1581 bp) containing a kanamycin selectable marker flanked by site-specific recombinase target sequences (FRT) was synthesized by PCR from plasmid pKD4 (Datsenko and Wanner, *Proc. Natl. Acad. Sci.* 97:6640-6645 (2000)) with primer pairs, T-kan(tyrA) (5'-AATTCATCAGGATCTGAACGGGC AGCTGACGGCTC GCGTGGCTTAAC GTCTTGAGCGATTGTGTAG-3') (SEQ ID NO:3) which contains a homology arm (underlined, 46 bp) chosen to match sequences in the upstream region of the aroF stop codon and a priming sequence (20 bp), and B-kan(trc) (5'-AAAACATTATCCAGAACGGGAGTGCGCCTTGAG CG ACACGAATATGA ATATCCTCCTTAGTTCC-3') (SEQ ID NO:4) that contains a homology arm (underlined, 42 bp) chosen to match sequences in the 5'-end region of the Ptrc promoter DNA fragment and a priming sequence (22 bp). A second linear DNA fragment (163 bp) containing a Ptrc promoter comprised of the −10 and −35 consensus sequences, lac operator (lacO), and ribosomal binding site (rbs) was synthesized by PCR from plasmid pTrc99A (Invitrogen, Carlsbad, Calif.) with primer pairs, T-trc(kan) (5'-CTAAGGAGGATATTCATATTCGTGTCGC TCA AGGC GCACT-3') (SEQ ID NO:5) that contains a homology arm (underlined, 18 bp) chosen to match sequences in the downstream region of the kan open reading frame and a priming sequence (22 bp), and B-trc(tyrA) (5'-CGACTTCATCAATTTGATCGCGTAATG CGGTCAATT CAGCAACCATG GTCTGTTTCCTGTGTGAAA-3') (SEQ ID NO:6) that contains a homology arm (underlined, 46 bp) chosen to match sequences in the downstream region of the tyrA start codon and a priming sequence (20 bp). The underlined sequences illustrate each respective homology arm, while the remainder is the priming sequences for hybridization to complementary nucleotide sequences on the template DNA for the PCR reaction.

Standard PCR conditions were used to amplify the linear DNA fragments using the MasterAmp™ Extra-Long PCR kit (Epicentre, Madison, Wis.) as follows. The PCR reaction mixture contained 1 µL of plasmid DNA, 25 µL of 2×PCR buffer #1, 1 µL of the 5'-primer (20 µM), 1 µL of the 3'-primer (20 µM), 0.5 µL of MasterAmp™ Extra-Long DNA polymerase, and 21.5 µL of sterilized, deionized $H_2O$. The PCR reaction conditions were: 94° C. for 3 min; 25 cycles of 93° C. for 30 sec, 55° C. for 1 min, and 72° C. for 3 min; followed by 72° C. for 5 min. After completing the PCR reactions, the PCR products were purified using the Mini-elute QIAquick Gel Extraction Kit™ (QIAGEN Inc. Valencia, Calif.). The DNA was eluted with 10 µL of distilled water by centrifuging twice at high speed. The concentration of the isolated PCR product was about 0.5-1.0 µg/µL.

E. coli MC1061 strain carrying a λ-Red recombinase expression plasmid was used as a host strain for the recombination of PCR fragments. This strain was constructed by transformation with a λ-Red recombinase expression plasmid, pKD46 (amp®) (Datsenko and Wanner, supra) into E. coli strain MC1061 (Coli Genetics Stock Center, Yale University, #6649). The λ-Red recombinase in pKD46 is comprised of three genes exo, bet, and gam, expressed under the control of an arabinose-inducible promoter. Transformants were selected on LB plates containing 100 µg/mL ampicillin at 30° C. The electro-competent cells of E. Coli MC1061 strain carrying pKD46 were prepared as follows. E. coli MC1061 cells carrying pKD46 were grown in SOB medium (Hanahan, *DNA Cloning: A Practical Approach*, D. M. Glover, ed., IRL Press, Washington, D.C., 1985, pp. 109-125) with 100 µg/mL ampicillin and 1 mM L-arabinose at 30° C. to an $OD_{600}$ of 0.5, followed by chilling on ice for 20 min. Bacterial cells were centrifuged at 4,500 rpm using a Sorvall® RT7 PLUS (Kendro Laboratory Products, Newton, Conn.) for 10 min at 4° C. After decanting the supernatant, the pellet was resuspended in ice-cold water and centrifuged again. This process was repeated twice and the cell pellet was resuspended in 1/100 volume of ice-cold 10% glycerol.

Both the kanamycin marker PCR products (~1 µg) and Ptrc promoter PCR products (~1 µg) were mixed with 50 µL of the competent cells and pipetted into a pre-cooled electroporation cuvette (0.1 cm) on ice. Electroporation was performed using a Gene Pulser System (Bio-Rad Laboratories, Hercules, Calif.) set at 1.8 kV, 25 µF with the pulse controller set at 200 ohms. SOC medium (1 mL) was added after electroporation. The cells were incubated at 37° C. for 1 h. Approximately one-half of the cells were spread on LB plates containing 25 µg/mL kanamycin. After incubating the plate at 37° C. overnight, six kanamycin resistant transformants were selected.

The chromosomal integration of both the kanamycin selectable marker and the Ptrc promoter in front of the tyrA gene was confirmed by PCR analysis. A colony of transformants was resuspended in 25 µL of PCR reaction mixture containing 23 µL of SuperMix (Invitrogen), 1 µL of 5'-primer T-ty(test) (5'-CAACCGCGCAGTGAAATGAAATACGG-3') (SEQ ID NO:7) and 1 µL of 3'-primer B-ty(test) (5'-GCGCTCCGGAACATAAATAGGCAGTC-3')(SEQ ID NO:8). The test primers were chosen to amplify regions located in the vicinity of the integration region. PCR analysis with the T-ty(test) and B-ty(test) primer pair revealed the expected size fragment, i.e., 1,928 bp on a 1% agarose gel. The resultant recombinant is designated herein as E. coli WS158.

Strain BNT565.2, prepared as described above, was then used as the recipient in another P1-mediated transduction with phage grown on E. coli strain WS158 that carries Ptrc-tyrA [KanR], a chromosomal modification resulting in the strong trc promoter driving tyrA expression. The pheA and tyrA genes are tightly linked on the chromosome, so selection was made for rare transductants that were resistant to both tetracycline and kanamycin. One such transductant was called DPD4009, which was shown to require phenylalanine for growth and to excrete tyrosine.

Construction of E. coli Strain DPD4512:

E. coli Strain DPD4512 was constructed by transformation of E. coli Strain DPD4009 using plasmid pCA16, which caries the *Rhodotorula glutinis* pal gene in pKK223-3 plasmid, and selection for ampicillin resistance. Plasmid pCA16 was prepared as follows. The *Rhodotorula glutinis* (ATCC No. 10788) pal gene, SEQ ID NO:1 (GenBank Accession no. M18261), was amplified from reverse-transcribed RNA that was purified from exponential phase cells grown in the complex medium containing phenylalanine. The gene sequence of pal from various sources, including *Rhodosporidium toruloides* also known as *Rhodotorula glutinis*, has been determined and published (Edwards et al., *Proc. Natl. Acad. Sci., USA* 82:6731-6735 (1985); Cramer et al., *Plant Mol. Biol.* 12:367-383 (1989); Lois et al., *EMBO J.* 8:1641-1648 (1989); Minami et al., *Eur. J. Biochem.* 185:19-25 (1989); Anson et al., *Gene* 58:189-199 (1987); Rasmussen & Oerum, *DNA Sequence*, 1:207-211 (1991)).

The *Rhodotorula glutinis* mRNA was reversed transcribed according to the Perkin Elmer (Norwich, Conn.) GeneAmp Kit instructions without diethylpyrocarbonate (DEPC) treated water. The primers used were the random hexamers supplied with the kit. Primers used to amplify the pal gene included the upstream primer 5'-ATAGTAGAATTCATG-GCACCCTCGCTCGACTCGA-3' (SEQ ID NO:9) containing an EcoRI restriction site, and a downstream PCR primer 5'-GAGAGACTGCAGAGAGGCAGCCAAGAACG-3' (SEQ ID NO:10) containing a PstI restriction site which were synthesized based on the *Rhodosporidium toruloides* pal gene. PCR fragments were digested with EcoRI and PstI and ligated to pKK223-3 previously cut with EcoRI and PstI forming pCA16.

Construction of E. coli Strain DPD4515:

Tyrosine producing strain E. coli DPD4515 was constructed by transformation of E. coli strain DPD4009 using plasmid pCL101 EA, which carries E. coli aroEACBL genes in pCL1920 (obtained from Central Bureau for Fungal Cultures, Baarn, The Netherlands), and selection for spectinomycin resistance. The pCL101 EA plasmid was constructed as described by Valle et al. in U.S. Patent Application Publication No. 2002/0155521 (in particular Example 7), which is incorporated herein by reference.

Construction of E. coli Strain DPD5040:

E. coli strain DPD5040 was constructed by transformation of E. coli Strain DPD4515 using plasmid pCA16, and selection for ampicillin resistance.

Construction of E. coli Strain DPD5013:

E. coli strain DPD5013 was constructed by transformation of E. coli Strain DPD4009 with pCL.PAL. Plasmid pCL.PAL was constructed by isolating the Ptac promoter-*R. glutinis* PAL gene cassette from pCA16 plasmid via BamHI and HindIII digestion, and subcloning into the BamHI and HindIII restriction sites in the polylinker of plasmid pCL1920. pCL.PAL carries a spectinomycin resistance gene, and it allows the expression of the *R. glutinis* PAL gene on a low copy plasmid.

Construction of E. coli Strain DPD5041:

E. coli Strain DPD5041 was constructed by transforming E. coli tyrosine producing strain DPD4515 with plasmid pLH276. Plasmid pLH276 was constructed from plasmid pLH273 as follows. Plasmid pLH273 contains a bacteriophage T5 promoter cassette cloned into plasmid pACYC184 (GenBank/EMBL Acc. No. X06403, available from New England Biolabs, Inc., Beverly, Mass.). The T5 promoter cassette was isolated from pQE70 (Qiagen, Valencia, Calif.) by XhoI-NheI digestion. This DNA fragment containing the T5 promoter followed by a multiple cloning site was ligated into plasmid pACYC184 digested by the compatible SalI and XbaI restriction enzymes to give plasmid pLH273. Plasmid pLH273 is a low copy stable expression vector with p15A origin of replication for the expression of proteins in *E. coli*.

Plasmid pLH276 was generated by PCR amplification of the pal gene from pCA16 using the 5' PCR primer of 5'-CTCGCTCGACTCGATCTCGCACTCGT-TCGCAAACG-3' (SEQ ID NO:11) and the 3' PCR primer of 5'-TTGAACTCGAACTCGATCGCGCGCAAGTCG-3' (SEQ ID NO:12) by Pfx DNA polymerase (Invitrogen, Carlsbad, Calif.). This PCR fragment was digested by SphI and HindIII restriction enzymes, and ligated into the SphI, HindIII digested pLH273 vector, to give pLH276. Plasmid pLH276 is an expression vector for *R. glutinis* PAL enzyme under the strong T5 promoter.

Construction of *E. coli* Strain DPD5047:

*E. coli* Strain DPD5047 was constructed by transforming *E. coli* strain BL21 (DE3) [genotype: recA1 endA1 hsdR17 supE44 thi-1 gyrA96 relA1 f80lacZ dM15 d(lacZYA-argF) U169 (DE3)], obtained from Stratagene (La Jolla, Calif.) with plasmid pCA16, which is described above. This strain expresses the PAL enzyme from *R. glutinis* in an *E. coli* B host.

HPLC Determination of Tyrosine, Phenylalanine, Calif., and pHCA:

Samples were analyzed for tyrosine (Tyr), phenylalanine (Phe), CA, and pHCA using reverse-phase chromatography with an Agilent HP1100 HPLC system equipped with an autosampler, diode-array detector, and ChemStation for data acquisition and processing (Agilent Technologies, Inc., Wilmington, Del.). The analyses were done using a 4.6 mm×15 cm Zorbax SB-C18 column (3.5 µm particle size), obtained from Agilent Technologies, Inc., thermostated at 35° C. The samples were run using a flow rate of 1.0 mL/min with an eight-minute solvent gradient from 5% acetonitrile/water, containing 0.1% trifluoroacetic acid, to 80% acetonitrile/water, containing 0.1% trifluoroacetic acid. A diode-array detector set at 210, 260, and 280 nm was used to detect the various compounds at their optimum absorbance wavelength.

The aqueous samples were diluted 1:3 with water before injection of 50 µL of the sample into the HPLC. A standard mixture of the analytes was prepared by mixing equal portions of solutions of the individual components, each at a concentration of 1 mg/mL.

Spectrophotometric Assay for PAL and TAL Activity:

The method used to determine tyrosine ammonia lyase activity and phenylalanine ammonia lyase activity is based on the method reported by Abell and Shen (*Methods Enzymol.* 142:242-248 (1987)). To determine PAL activity, the reaction was initiated by adding cell free extract to a solution containing 1 mM L-phenylalanine in 50 mM Tris-HCl (pH 8.5) buffer. The reaction was followed spectrophotometrically by monitoring the absorbance of the product, cinnamate, at 290 nm using a molar extinction coefficient of 9000 $cm^{-1}$. The assay was run over a 3 min period using an amount of enzyme that produced a change in absorbance in the range of 0.0075 to 0.018/min. One unit of activity is defined as the amount of enzyme that deaminates 1 µmol of phenylalanine to cinnamate per min.

TAL activity was measured similarly with tyrosine replacing phenylalanine in the reaction solution. The absorbance of the para-hydroxycinnamate produced was followed at 315 nm with an extinction coefficient of 10,000 $cm^{-1}$. One unit of activity is defined as the amount of enzyme that deaminates 1 pmol of tyrosine to para-hydroxycinnamate per min. With the *R. glutinis* enzyme, we found that TAL activity was ⅙ of the PAL activity and in many cases we estimated the TAL activity from the PAL activity measurement.

Examples 1-12

The Effect of pH on the Production of pHCA in Two-Stage Fermentations

The purpose of these Examples was to demonstrate the effect of increasing the pH during fermentation on the production of pHCA by various recombinant strains. In these Examples the fermentation was carried out at an initial pH of 6.5 to 7.0 and the pH was changed at a time during the fermentation to a pH from 6.1 to 9.7.

The strains used in these Examples were *E. coli* DPD5013, *E. coli* DPD4512, and *E. coli* DPD5040, constructed as described above. These strains are recombinant *E. coli* strains that were designed for overproduction of tyrosine and conversion of the tyrosine produced to pHCA by the inclusion of the pal gene from *R. glutinis*. Phenylalanine was produced as a side product in these runs and was converted to CA by the PAL activity.

Fermentation Protocol:

The pre-seed culture was a frozen culture of the desired recombinant *E. coli* strain. The seed culture was grown for approximately 15 h in a 2 L flask with 500 mL of seed medium, incubated in a gyrotory shaker (New Brunswick Scientific, Edison, N.J.), at 300 rpm and 35° C. The seed medium consisted of $KH_2PO_4$ (1 g/L), $Na_2HPO_4$ (3 g/L), $(NH_4)_2SO_4$ (3 g/L), $MgSO_4 \cdot 7H_2O$ (0.3 g/L), yeast extract (1 g/L), MOPS (15.7 g/L), L-phenylalanine (10 mg/L). The pH was adjusted to 6.8 using NaOH. Glucose and spectinomycin were added aseptically to give final concentrations of 10 g/L and 50 mg/L, respectively.

The fermentations were done in a 14 L Braun Fermentor, Biostat C.B. (Braun Biotech International, Melesungen, Germany). The fermentation medium consisted of the following in a 7.5 L volume: $KH_2PO_4$ (7 g), $Na_2HPO_4$ (17 g), $MgSO_4 \cdot 7H_2O$ (4 g), $(NH_4)_2SO_4$ (8 g), thiamine (8 mg), phenylalanine (320 mg), and Mazu DF204 Defoamer (8 mL) with the pH adjusted to 6.5. For *E. coli* strains DPD4512 and DPD5040, 5 g/L yeast extract was added to the fermentation medium and the initial pH was 7.0. After sterilization of the fermentation medium, 267 g of glucose solution (60% w/w), 160 mL of trace elements, and 8 mL of spectinomycin (50 mg/mL) were added aseptically. The composition of the trace elements solution is given in Table 1.

TABLE 1

| Trace Elements Solution | |
|---|---|
| Chemical | Concentration (g/L) |
| Citric acid | 10 |
| $CaCl_2 \cdot 2H_2O$ | 1.5 |
| $FeSO_4 \cdot 7H_2O$ | 5 |
| $ZnSO_4 \cdot 7H_2O$ | 0.39 |
| $CuSO_4 \cdot 5H_2O$ | 0.38 |
| $CoCl_2 \cdot 6H_2O$ | 0.2 |
| $MnCl_2 \cdot 4H_2O$ | 0.3 |

The dissolved oxygen concentration was controlled at 25% of air saturation with a cascade of agitation from 400 to 1500 rpm and aeration followed from 2 to 10 SLPM. The temperature was controlled at 35° C. and the head pressure was 50 kPa. The pH was controlled at 6.5 or 7 with 20% w/v $H_3PO_4$ and 40% w/v $NH_4OH$. The fermentation was done in a fed-batch mode with the addition of glucose (60% w/w). The glucose feed was initiated when the concentration dropped below 4 g/L. The following formula was used to calculate the glucose feed rate in g/min: $OD_{550} \times$Ferm. wt.$\times 0.001762$. When the glucose concentration exceeded 0.5 g/L, the glucose feed rate was reduced to maintain the glucose concentration below 0.5 g/L. IPTG was added to a concentration of 1 mM when the culture density reached an $OD_{550}$ between 8 and 10.

After a specific time, the pH was changed as shown in Table 2. Whenever the pH change was above 0.4 units, it was done intermittently in several step changes with a change of 0.4 pH units every 2 h. The pH was changed by addition of 50% w/v KOH. Samples were taken at various times and the concentration of pHCA, CA, Phe, and Tyr in the culture were determined using HPLC, as described above. The pHCA concentrations determined after 72 h are shown in Table 2.

pHCA using recombinant *E. coli* strains containing a TAL enzyme activity. The protocols used to produce cultures having TAL activity were described in Examples 1-12.

Samples of cell culture broth (10 mL portions) from Example 8 containing *E. coli* strain PD4512 was distributed into 125 mL baffled flasks, L-Tyr was added to a concentration of 10 g/L, and the pH of was adjusted to various values with concentrated KOH or $H_2SO_4$.

The flasks were incubated in an incubator shaker (Innova 4000, New Brunswick Co.) at 35° C. and 300 rpm. At various times, samples were taken and analyzed for pHCA using HPLC, as described above. The pH conditions and the concentration of pHCA produced are summarized in Table 3 (Reference No. FL-2003-16).

TABLE 2

Summary of pH Changes and the Amount of pHCA Produced

| Example | Run No. | Strain | pH Change | Time of pH Change, h | pHCA, g/L |
|---|---|---|---|---|---|
| 1, Comparative | pHCA152 & 155 | *E. coli* DPD5013 | 6.1 | 24 | 0.50* |
| 2, Comparative | pHCA151 & 154 | *E. coli* DPD5013 | 6.5 | 24 | 0.60* |
| 3, Comparative | pHCA155 & 156 | *E. coli* DPD5013 | 6.9 | 24 | 1.25* |
| 4, Comparative | pHCA157 & 161 | *E. coli* DPD5013 | 7.0 | 24 | 1.25* |
| 5, Comparative | pHCA158 & 162 | *E. coli* DPD5013 | 7.5 | 24 | 1.65* |
| 6 | pHCA159 & 163 | *E. coli* DPD5013 | 8.0 | 24 | 1.95* |
| 7 | pHCA160 | *E. coli* DPD5013 | 8.4 | 24 | 1.7 |
| 8, Comparative | pHCA174 | *E. coli* DPD4512 | 7.5 | 44 | 4.7 |
| 9 | pHCA175 | *E. coli* DPD4512 | 8.0 | 44 | 5.51 |
| 10 | pHCA176 | *E. coli* DPD4512 | 8.3 | 44 | 5.8 |
| 11, Comparative | pHCA180 | *E. coli* DPD5040 | 7.0 | 60 | 5.0 |
| 12 | pHCA188 | *E. coli* DPD5040 | 9.7 | 60 | 5.8* |

*Average of two runs

Figure 2:
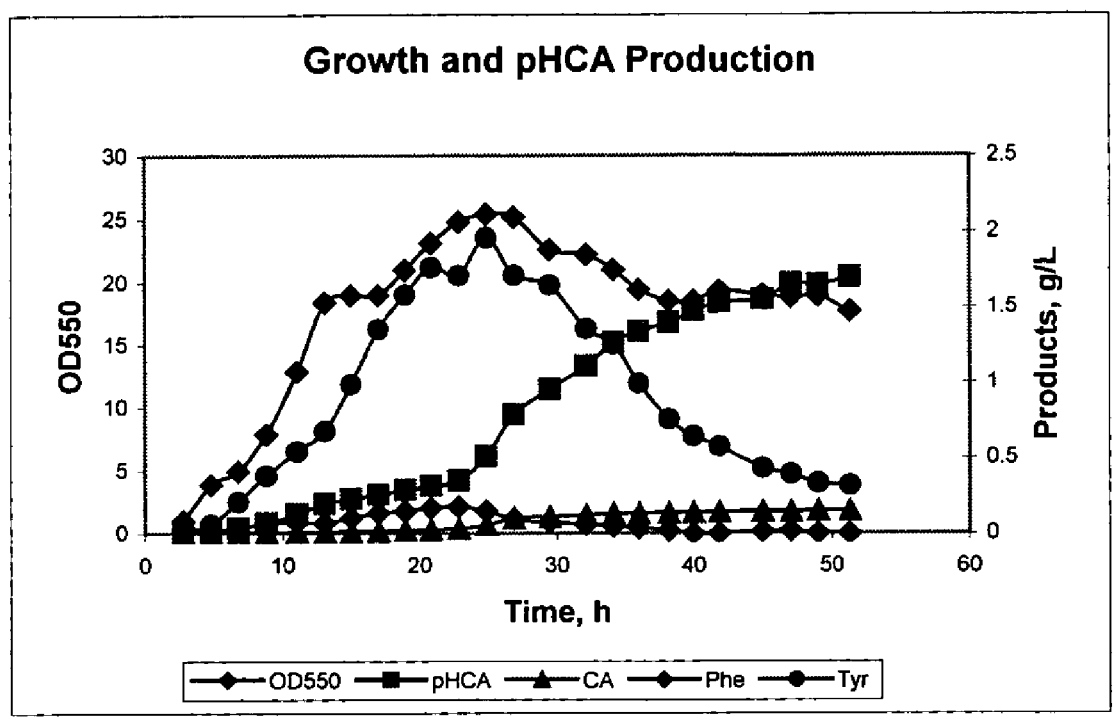
FIG. 2 shows the growth and pHCA production in a fermentation wherein the pH is changed to 8.4 after 24 hours.

As can be seen from the results shown in Table 2, changing the pH during the run had a significant effect on pHCA production. An example of pHCA production without a pH change is shown in FIG. 1. The pHCA and Tyr production was almost constant between 9 to 72 h, ending at a concentration of 1.3 g/L pHCA and 7 g/L Tyr. An example of the results obtained with a pH change to 8.4 is shown in FIG. 2. At the time of the pH change, a steep increase in pHCA production and a steep decline in Tyr concentration was observed, ending at a concentration of 1.7 g/L pHCA and 0.3 g/L Tyr. The enhancement of pHCA production at higher pH may be due to mitigation of pHCA toxicity at pH 6.1 to 7.5, and to enhancement of TAL activity and improved Tyr accessibility to the enzyme at a pH above 7.8.

These results demonstrate the enhanced production of pHCA by recombinant strains of *E. coli* in a two-stage fermentation wherein the pH is increased to alkaline values during the fermentation.

Examples 13-17

Effect of pH on the Biocatalytic Conversion of Tyrosine to pHCA (Study #FL-2003-16)

The purpose of these Examples was to demonstrate the effect of pH on the biocatalytic conversion of tyrosine to

TABLE 3

Effect of pH on the Biocatalytic Conversion of Tyrosine to pHCA

| Example | Strain | pH | Incubation Time, h | pHCA*, mM |
|---|---|---|---|---|
| 13, Comparative | *E. coli* DPD4512 | 7.4 | 1 | 0.40 |
| 14 | *E. coli* DPD4512 | 8.2 | 1 | 1.18 |
| 15 | *E. coli* DPD4512 | 8.96 | 1 | 8.05 |
| 16 | *E. coli* DPD4512 | 9.74 | 1 | 40.30 |
| 17 | *E. coli* DPD4512 | 11.17 | 1 | 1.40 |

*Average of two runs

As can be seen from the results in Table 3, raising the pH to alkaline values increased the pHCA production rate significantly. The optimum pH for the biocatalytic conversion is estimated to be between 9.5 and 10.5.

Similar studies were done at various temperatures up to 45° C. The initial rates of the conversion were enhanced at temperatures between 40 and 45° C.; however, the PAL/TAL enzyme lost activity over time at the higher temperatures. Consequently, the pHCA yield was not improved at these temperatures.

Examples 18-20

Production of pHCA in a Two-Stage Process Consisting of Fermentation to Tyrosine and Biocatalytic Conversion to pHCA The purpose of these Examples was two demonstrate the production of pHCA via a two-stage process consisting of fermentation to produce tyrosine, and subsequent biocatalytic conversion of tyrosine to pHCA using different amounts of cells. After the fermentation to tyrosine, cells having a TAL activity were added to the fermentation medium and the pH was adjusted to 10.0.

Fermentation to Produce Tyrosine

The strain used in this Example was *E. coli* DPD4515. The protocols for seed culture production and fermentation were similar to those described in Examples 1-12.

During the fermentation, the dissolved oxygen concentration was controlled at 25% of air saturation with a cascade of agitation that followed with aeration. Agitation varied from 500 to 1500 rpm and aeration from 2 to 8 SLPM. The head pressure was controlled at 50 kPa. The pH was maintained at 6.8 with the addition of $NH_4OH$ (40% w/v) initially, KOH (50% w/v) after 45 h, and acid titration with $H_3PO_4$ (20% w/v). Glucose feed was started with a 60% w/w glucose solution when the concentration fell below 4 g/L. The glucose feed rate was calculated using the following formula for the first 40 h: feed rate g/min=$OD_{550}$×Ferm. wt.×0.003084, after 40 h the formula used was feed rate g/min=$OD_{550}$×Ferm. wt.×0.001762. A lower glucose feed rate was used if glucose accumulated above 0.5 g/L. IPTG was added to a concentration of 1.0 mM when the culture reached an $OD_{550}$ between 8 and 10. The fermentation was terminated at 72 h. Three fermentation runs as described above were run in parallel (pHCA212, -213, & -214). Samples were removed at various times during the fermentation and the tyrosine (Tyr) and phenylalanine (Phe) concentrations were determined using HPLC, as described above. The results for one such run are given in Table 4 (Run No. pHCA212).

TABLE 4

Tyrosine and Phenylalanine Production

| Time, h | $OD_{550}$ | Phe, g/L | Tyr, g/L |
|---|---|---|---|
| 2.7 | 3.1 | 0.2 | 0.1 |
| 4.6 | 9.0 | 0.1 | 0.2 |
| 6.7 | 14.7 | 0.1 | 0.5 |
| 8.0 | 21.2 | 0.1 | 0.9 |
| 9.7 | 22.5 | 0.2 | 1.5 |
| 11.7 | 28.1 | 0.1 | 1.9 |
| 13.6 | 33.0 | 0.1 | 1.8 |
| 15.7 | 42.2 | 0.1 | 1.7 |
| 17.7 | 48.4 | 0.1 | 3.4 |
| 19.6 | 51.6 | 0.1 | 4.4 |
| 21.7 | 59.2 | 0.1 | 5.1 |
| 23.7 | 62.4 | 0.1 | 6.3 |
| 25.2 | 74.4 | 0.1 | 7.3 |
| 27.1 | 76.0 | 0.2 | 8.3 |
| 29.0 | 86.8 | 0.2 | 9.8 |
| 30.7 | 91.2 | 0.3 | 10.8 |
| 32.5 | 91.2 | 0.6 | 13.7 |
| 34.6 | 88.8 | 0.5 | 12.3 |
| 37.5 | 88.0 | 0.8 | 15.1 |
| 39.6 | 86.0 | 0.9 | 15.1 |
| 41.5 | 79.6 | 1.0 | 15.4 |
| 43.6 | 78.8 | 1.1 | 16.1 |
| 45.4 | 78.4 | 1.1 | 16.5 |
| 48.1 | 82.0 | 1.2 | 16.8 |
| 50.1 | 84.8 | 1.3 | 16.9 |
| 52.0 | 80.4 | 1.3 | 17.2 |
| 54.0 | 80.8 | 1.3 | 16.9 |
| 56.0 | 84.0 | 1.4 | 16.8 |
| 58.2 | 80.8 | 1.4 | 17.3 |
| 60.0 | 77.2 | 1.6 | 18.5 |
| 62.1 | 83.6 | 1.5 | 18.9 |
| 64.0 | 75.2 | 1.4 | 18.9 |
| 66.8 | 73.6 | 1.4 | 18.6 |
| 70.0 | 68.8 | 1.5 | 19.3 |
| 71.9 | 76.4 | 1.6 | 19.3 |

After 72 h, Tyr and Phe accumulated to concentrations of 19.3 and 1.6 g/L respectively.

Biocatalytic Conversion of Tyrosine to pHCA:

The fermentation broths were reduced in volume to 5 L in their original fermentors. Frozen cells paste obtained from the fermentation of *E. coli* DPD5040, as described in Example 11, was thawed and divided into three fractions, 276 g, 92 g and 27.6 g. Each fraction was suspended to homogeneity in 0.5 L of cold 0.05 M potassium phosphate buffer at pH 10.0 and each of the suspensions was pumped into the corresponding fermentor. The pH was controlled at 10.0 by the addition of KOH (50% w/v) and $H_3PO_4$ (20% w/v). Samples were taken at various times for determination of Tyr, Phe, pHCA and CA using HPLC, as described above. The results for the three runs are presented in Table 5.

TABLE 5

Biocatalytic Production of pHCA and CA

| Example | Amount of Cells, g wet wt | Run No. | Time, h | pHCA, g/L | CA, g/L | Phe, g/L | Tyr, g/L |
|---|---|---|---|---|---|---|---|
| 18 | 276 | pHCA216 | 2.8 | 13.7 | 0.88 | 0.27 | 1.10 |
|  | 276 |  | 4.8 | 15.7 | 0.94 | 0 | 0.25 |
|  | 276 |  | 6.8 | 15.5 | 0.92 | 0 | 0.14 |
|  | 276 |  | 8.8 | 14.7 | 0.89 | 0 | 0.12 |
|  | 276 |  | 16.6 | 17.3 | 1.07 | 0 | 0.11 |
| 19 | 92 | pHCA217 | 2.8 | 7.9 | 0.88 | 0.56 | 9.67 |
|  | 92 |  | 4.8 | 9.9 | 0.86 | 0.00 | 5.69 |
|  | 92 |  | 6.8 | 13.4 | 1.01 | 0.00 | 4.07 |
|  | 92 |  | 8.8 | 13.9 | 0.93 | 0.42 | 2.40 |
|  | 92 |  | 16.6 | 16.8 | 1.03 | 0.00 | 0.34 |
| 20 | 27.6 | pHCA219 | 2.8 | 3.1 | 0.45 | 0.67 | 15.73 |
|  | 27.6 |  | 4.8 | 4.5 | 0.54 | 0.52 | 13.66 |
|  | 27.6 |  | 6.8 | 5.5 | 0.60 | 0.41 | 11.99 |
|  | 27.6 |  | 8.8 | 6.6 | 0.66 | 0.29 | 11.31 |
|  | 27.6 |  | 16.6 | 9.0 | 0.71 | 0 | 7.96 |
|  | 27.6 |  | 24.7 | 11.2 | 0.72 | 0 | 4.39 |
|  | 27.6 |  | 36.6 | 13.0 | 0.74 | 0 | 1.93 |
|  | 27.6 |  | 48.0 | 14.9 | 0.79 | 0 | 1.12 |

The results show that the amount of pHCA and CA produced increased with time and that the bioconversion rate was faster with higher amounts of cells carrying PAL/TAL activity.

A similar procedure was used to produce PAL/TAL enzyme for biocatalytic studies with various strains and the appropriate antibiotics. In a typical process, cells were harvested at 55-65 h to yield 400-600 g of wet cell paste. Typical activities in *E. coli* DPD5040 were 120-600 units of PAL per gram of protein and 20-100 units of TAL per gram of protein. The activities in *E. coli* DPD5041 grown at the same conditions were 12-36 units of PAL per gram of protein and 2-6 units of TAL per gram of protein, and in *E. coli* DPD5047, the activities were 120 units of PAL per gram of protein and 20 units of TAL per gram of protein. Biocatalytic conversion of Tyr to pHCA can be conveniently done with 10-500 units/L of TAL, and conversion of Phe to CA can be done with 60-3000 units/L of PAL.

Examples 21-27

The Effect of pH on the Biocatalytic Conversion of Phenylalanine to Cinnamic Acid (Experiment #FL-2004-12)

The purpose of these Examples was to demonstrate the effect of pH on the conversion of phenylalanine to CA using a recombinant *E. coli* strain containing a PAL enzyme activity.

These studies were done using 50 mL reaction mixtures containing 0.075 M CAPS buffer, 21 g/L wet cells (*E. coli* DPD5047), 7 g/L phenylalanine, obtained from Sigma Chemical Co., with the pH between 8 and 11, as specified in Table 6, in 250 mL baffled flasks.

The flasks were incubated in an incubator shaker (Innova 4000, New Brunswick Co.) at 35° C. and 300 rpm. At 1.5 h samples were taken and analyzed for CA using HPLC, as described above. The pH conditions and the concentration of pHCA produced are summarized in Table 6. The results suggest that the optimum pH for conversion of Phe to CA is between 9.5 and 10.5.

TABLE 6

Effect of pH on the Biocatalytic Conversion of Phenylalanine to CA

| Example | pH* | CA**, mM |
|---------|------|----------|
| 21, Comparative | 7.9 | 2.55 |
| 22 | 8.4 | 3.8 |
| 23 | 8.8 | 3.95 |
| 24 | 9.35 | 4.4 |
| 25 | 9.8 | 5.1 |
| 26 | 10.25 | 6.5 |
| 27 | 10.8 | 6.2 |

*The pH is the average between the initial and final pH of two runs. A pH decrease of 0.1 to 0.4 pH units was observed at the time of sampling.
**Average of two runs.

Example 28

The Effect of Ammonium Ion on the Conversion of Tyrosine to pHCA (Experiment #FL-2004-11)

The purpose of this Example was to demonstrate the inhibitory effect of ammonium ion concentration on the biocatalytic conversion of tyrosine to pHCA.

These studies were done using 50 mL reaction mixtures in 250 mL baffled flasks. The reaction mixture contained 0.1 M CAPS buffer, 61 g/L of wet cells (*E. coli* DPD5047), 46.5 g/L tyrosine, obtained from Sigma Chemical Co. or J.T. Baker (Phillipsburg, N.J.), and $NH_4Cl$ at various concentrations. The pH was adjusted to 10.0 with KOH. The flasks were incubated in an incubator shaker (Innova 4000, New Brunswick Co.) at 35° C. and 300 rpm. The pH in reaction mixtures was adjusted daily to pH 10.0 with KOH. Samples were taken at 24 and 72 h and the pHCA concentration was determined using HPLC, as described above.

The results are summarized in Table 7. As can be seen from the data in the Table, ammonium ion was inhibitory at concentrations above about 100 mM, and a 20% reduction in pHCA production was observed at an ammonium ion concentration of 400 mM.

TABLE 7

Effect of Ammonium Ion on the Biocatalytic Conversion of Tyrosine to pHCA

| $NH_4Cl$ added, mM | pHCA*, mM 24 h | pHCA*, mM 72 h |
|---|---|---|
| 0 | 132 | 292 |
| 25 | 138 | 301 |
| 50 | 134 | 295 |
| 100 | 128 | 286 |
| 200 | 127 | 279 |
| 400 | 117 | 221 |

*Average of two runs

Example 29

Production of pHCA in a Two-Step Process Consisting of Fermentation to Tyrosine and Biocatalytic Conversion to pHCA The purpose of this prophetic Example is to describe the production of pHCA via a two-step process consisting of fermentation to produce tyrosine, which is then isolated from the growth medium, and the subsequent biocatalytic conversion of the isolated tyrosine to pHCA.

Tyrosine is produced by fermentation using *E. coli* DPD4515, as described in Examples 18-20. The fermentation is stopped after 72 h and the tyrosine is separated from the fermentation broth using low speed centrifugation. The resulting precipitate is suspended in water and separated again using low speed centrifugation. Then, the tyrosine is added back to the fermentor, which is filled with about 7.5 kg of water and the pH is adjusted to 10.0 using 50% w/w sodium hydroxide. Frozen cell paste from the fermentation of *E. coli* DPD5040, as described in Example 11, is thawed and 250 g is suspended to homogeneity in 0.5 L of cold 0.05 M potassium phosphate buffer at pH 10.0. The cell suspension is pumped into the fermentor. The fermentor is operated at 35° C. and 600 rpm and the pH is controlled at 10.0 by the addition of sodium hydroxide (50% w/w) and $H_3PO_4$ (20% w/v). The biocatalytic reaction is allowed to proceed for 16 h, producing pHCA, which accumulates in the reaction medium. The pHCA-containing medium is centrifuged and the solids are discarded. The supernatant is transferred to the fermentor, operated at 35° C. and 600 rpm. The pH of the solution is adjusted to 9.0 using 20% w/v sulfuric acid. Then, 0.254 mL of Alcalase® (which may be obtained from Novozymes, Krogshoejvej 36, 2880 Bagsvaerd, Denmark) and 0.134 g of Bromelain (Acros Organics, which may be obtained from Fisher Scientific, Pittsburgh, Pa.) are added. After a 1 h incubation, the solution is titrated to pH 2.2 with 20% w/v to precipitate the pHCA. The resulting suspension is centrifuged and the pHCA is recovered as a wet cake.

What is claimed is:

1. A method for the production of para-hydroxycinnamic acid comprising:
   (i) providing an *E. coli* host cell which:
      a) overproduces tyrosine when grown with a fermentable carbon substrate; and
      b) comprises an exogenous gene encoding a polypeptide having tyrosine ammonia lyase activity operably linked to suitable regulatory sequences wherein the polypeptide comprises the amino acid sequence as set forth in SEQ ID NO:2;
   (ii) contacting the *E. coli* host cell of (i) with a fermentable carbon substrate in a growth medium at physiological pH such that tyrosine accumulates in the growth medium;
   (iii) raising the pH of the growth medium to a pH of about 9 to a pH of about 10 such that tyrosine is converted to para-hydroxycinnamic acid, which accumulates to a concentration of at least 4.5 g/L; and
   (iv) optionally recovering said para-hydroxycinnamic acid.

2. A method according to claim 1 wherein the gene encoding a polypeptide having tyrosine ammonia lyase activity is under the control of an inducible promoter.

3. A method according to claim 1 wherein at step (iii) tyrosine ammonia lyase is added to the growth medium.

4. A method according to claim 1 wherein the pH of the growth medium is raised to a pH of about 9.5 to about 10.5.

5. A method according to claim 1 wherein said fermentable carbon substrate is selected from the group consisting of monosaccharides, oligosaccharides, polysaccharides, carbon dioxide, methanol, formaldehyde, formate, and carbon-containing amines.

6. A method according to claim 5 wherein said fermentable carbon substrate is glucose.

7. A method according to claim 1 wherein ammonia is removed from the growth medium.

* * * * *

SEQUENCE LISTING

<160> NUMBER OF SEQ ID NOS: 12

<210> SEQ ID NO 1
<211> LENGTH: 2703
<212> TYPE: DNA
<213> ORGANISM: Rhodotorula glutinis

<400> SEQUENCE: 1

```
atggcaccct cgctcgactc gatctcgcac tcgttcgcaa acggcgtcgc atccgcaaag      60
caggctgtca atggcgcctc gaccaacctc gcagtcgcag gctcgcacct gccccacaac     120
ccaggtcacg caggtcgaca tcgtcgagaa gatgctcgcc gcgccgaccg actcgacgct     180
cgaactcgac ggctactcgc tcaacctcgg agacgtcgtc tcggccgcga ggaagggcag     240
gcctgtccgc gtcaaggaca gcgacgagat ccgctcaaag attgacaaat cggtcgagtt     300
cttgcgctcg cagtgagagt cgtgctttcg ttctctggcg tcgagagggc gggaccttcc     360
caagttgcca agggactgac tgtcgctctc ctgtgtcgcg cagactctcc atgagcgtct     420
acggcgtcac gactggattt gcggatccg cagacacccg caccgaggac gccatctcgc      480
tccagaaggc gtgcgtcctc ctcgtctccc tctcgcttct cgagcttcgg actgaccgtc     540
ttcccgcaca gtctcctcga gcaccagctc tgccgtgttc tcccttcgtc gttcgactcg     600
ttccgcctcg gccgcggtct cgagaactcg cttcccctcg aggttgttcg cggcgccatg     660
acaatccgcg tcaacagctt gacccggtga gttgccgtcc ttactcactc agcggtcttc     720
gagctgacag ttggcgcacc cagcggccac tcggctgtcc gcctcgtcgt cctcgaggcg     780
ctcaccaact tcctcaacca cggcatcacc cccatcgtcc cctccgcgg caccatctct      840 gcgtcgggcg acctctctcc tctctcctac attgcagcgg ccatcagcgg tcacccggac     900
agcaaggtgc acgtcgtcca cgagggcaag gagaagatcc tgtacgcccg cgaggcgatg     960
gcgctcttca acctcgagcc cgtcgtcctc ggcccgaagg aaggtctcgg tctcgtcaac    1020
ggcaccgccg tctcagcatc gatggccacc ctcgctctgc acgacgcaca catgctctcg    1080
ctcctctcgc agtcgctcac ggccatgacg gtcgaagcga tggtcggcca cgccggctcg    1140
ttccacccct tccttcacga cgtcacgcgc cctcacccga cgcagatcga agtcgcggga    1200
aacatccgca agtcctcgga gggaagccgc tttgctgtcc accatgagga ggaggtcaag    1260
gtcaaggacg acgagggcat tctccgccag gaccgctacc ccttgcgcac gtctcctcag    1320
gtgcgcttac ttctgtttgt tctgccgaag acatgacgct gacgtccgct tactcgcgca    1380
gtggctcggc ccgctcgtca gcgacctcat tcacgcccac gccgtcctca ccatcgaggc    1440
cggccagtcg acgaccgaca accctctcat cgacgtcgag aacaagactt cgcaccacgg    1500
cggcaatttc caggctgccg ctgtggccaa caccatggag aagactcggt gcgccgcttc    1560
actgtgacct gttctcttgg tctcgtcctg acgagtacgc tgtgcagcct cgggctcgcc    1620
cagatcggca agctcaactt cacgcagctc accgagatgc tcaacgccgg catgaaccgc    1680 ggcctccccct cctgcctcgc ggccgaagac ccctcgctct cctaccactg caagggcctc    1740
gacatcgccg ctgcggcgta cacctcggag ttgggacacc tcgccaaccc tgtgacgacg    1800
catgtccagc cggctgagat ggcgaaccag gcggtcaact cgcttgcgct catctcggct    1860
cgtcgcacga ccgagtccaa cgacgtcctt tctctcgtga gtcaggcgct catcacactc    1920
gcgaacagaa gctgacgcac tcggtctcgc agctcctcgc cacccacctc tactgcgttc    1980
tccaagccat cgacttgcgc gcgatcgagt tcgagttcaa gaagcagttc ggcccagcca    2040
```

-continued

```
tcgtctcgct catcgaccag cactttggct ccgccatgac cggctcgaac ctgcgcgacg    2100
agctcgtcga gaaggtgaac aagacgctcg ccaagcgcct cgagcagacc aactcgtacg    2160
acctcgtccc gcgctggcac gacgccttct ccttcgccgc cggcaccgtc gtcgaggtcc    2220
tctcgtcgac gtcgctctcg ctcgccgccg tcaacgcctg gaaggtcgcc gccgccgagt    2280
cggccatctc gctcacccgc caagtccgcg agaccttctg gtccgccgcg tcgacctcgt    2340
cgcccgcgct ctcgtacctc tcgccgcgca ctcagatcct ctacgccttc gtccgcgagg    2400
agcttggcgt caaggcccgc cgcggagacg tcttcctcgg caagcaagag gtgacgatcg    2460
gctcgaacgt ctccaagatc tacgaggcca tcaagtcggg caggatcaac aacgtcctcc    2520
tcaagatgct cgcttagaca ctcttcccac tctcgcatcc cttccatacc ctatcccgcc    2580
tgcacttctt aggactcgct tcttgtcgga ctcggatctc gcatcgcttc tttcgttctt    2640
ggctgcctct ctagaccgtg tcggtattac ctcgagattg tgaatacaag cagtacccat    2700
cca                                                                  2703
```

<210> SEQ ID NO 2
<211> LENGTH: 716
<212> TYPE: PRT
<213> ORGANISM: Rhodotorula glutinis

<400> SEQUENCE: 2

```
Met Ala Pro Ser Leu Asp Ser Ile Ser His Ser Phe Ala Asn Gly Val
1               5                   10                  15

Ala Ser Ala Lys Gln Ala Val Asn Gly Ala Ser Thr Asn Leu Ala Val
            20                  25                  30

Ala Gly Ser His Leu Pro Thr Thr Gln Val Thr Gln Val Asp Ile Val
        35                  40                  45

Glu Lys Met Leu Ala Ala Pro Thr Asp Ser Thr Leu Glu Leu Asp Gly
    50                  55                  60

Tyr Ser Leu Asn Leu Gly Asp Val Val Ser Ala Arg Lys Gly Arg
65                  70                  75                  80

Pro Val Arg Val Lys Asp Ser Asp Glu Ile Arg Ser Lys Ile Asp Lys
                85                  90                  95

Ser Val Glu Phe Leu Arg Ser Gln Leu Ser Met Ser Val Tyr Gly Val
            100                 105                 110

Thr Thr Gly Phe Gly Gly Ser Ala Asp Thr Arg Thr Glu Asp Ala Ile
        115                 120                 125

Ser Leu Gln Lys Ala Leu Leu Glu His Gln Leu Cys Gly Val Leu Pro
    130                 135                 140

Ser Ser Phe Asp Ser Phe Arg Leu Gly Arg Gly Leu Glu Asn Ser Leu
145                 150                 155                 160

Pro Leu Glu Val Val Arg Gly Ala Met Thr Ile Arg Val Asn Ser Leu
                165                 170                 175

Thr Arg Gly His Ser Ala Val Arg Leu Val Val Leu Glu Ala Leu Thr
            180                 185                 190

Asn Phe Leu Asn His Gly Ile Thr Pro Ile Val Pro Leu Arg Gly Thr
        195                 200                 205

Ile Ser Ala Ser Gly Asp Leu Ser Pro Leu Ser Tyr Ile Ala Ala Ala
    210                 215                 220

Ile Ser Gly His Pro Asp Ser Lys Val His Val Val His Glu Gly Lys
225                 230                 235                 240

Glu Lys Ile Leu Tyr Ala Arg Glu Ala Met Ala Leu Phe Asn Leu Glu
                245                 250                 255
```

-continued

Pro Val Val Leu Gly Pro Lys Glu Gly Leu Val Asn Gly Thr
                260                 265                 270

Ala Val Ser Ala Ser Met Ala Thr Leu Ala Leu His Asp Ala His Met
            275                 280                 285

Leu Ser Leu Ser Gln Ser Leu Thr Ala Met Thr Val Glu Ala Met
290                 295                 300

Val Gly His Ala Gly Ser Phe His Pro Phe Leu His Asp Val Thr Arg
305                 310                 315                 320

Pro His Pro Thr Gln Ile Glu Val Ala Gly Asn Ile Arg Lys Leu Leu
                325                 330                 335

Glu Gly Ser Arg Phe Ala Val His His Glu Glu Val Lys Val Lys
            340                 345                 350

Asp Asp Glu Gly Ile Leu Arg Gln Asp Arg Tyr Pro Leu Arg Thr Ser
                355                 360                 365

Pro Gln Trp Leu Gly Pro Leu Val Ser Asp Leu Ile His Ala His Ala
    370                 375                 380

Val Leu Thr Ile Glu Ala Gly Gln Ser Thr Thr Asp Asn Pro Leu Ile
385                 390                 395                 400

Asp Val Glu Asn Lys Thr Ser His His Gly Gly Asn Phe Gln Ala Ala
                405                 410                 415

Ala Val Ala Asn Thr Met Glu Lys Thr Arg Leu Gly Leu Ala Gln Ile
            420                 425                 430

Gly Lys Leu Asn Phe Thr Gln Leu Thr Glu Met Leu Asn Ala Gly Met
        435                 440                 445

Asn Arg Gly Leu Pro Ser Cys Leu Ala Ala Glu Asp Pro Ser Leu Ser
    450                 455                 460

Tyr His Cys Lys Gly Leu Asp Ile Ala Ala Ala Tyr Thr Ser Glu
465                 470                 475                 480

Leu Gly His Leu Ala Asn Pro Val Thr Thr His Val Gln Pro Ala Glu
            485                 490                 495

Met Ala Asn Gln Ala Val Asn Ser Leu Ala Leu Ile Ser Ala Arg Arg
        500                 505                 510

Thr Thr Glu Ser Asn Asp Val Leu Ser Leu Leu Ala Thr His Leu
            515                 520                 525

Tyr Cys Val Leu Gln Ala Ile Asp Leu Arg Ala Ile Glu Phe Glu Phe
    530                 535                 540

Lys Lys Gln Phe Gly Pro Ala Ile Val Ser Leu Ile Asp Gln His Phe
545                 550                 555                 560

Gly Ser Ala Met Thr Gly Ser Asn Leu Arg Asp Glu Leu Val Glu Lys
                565                 570                 575

Val Asn Lys Thr Leu Ala Lys Arg Leu Glu Gln Thr Asn Ser Tyr Asp
            580                 585                 590

Leu Val Pro Arg Trp His Asp Ala Phe Ser Phe Ala Ala Gly Thr Val
        595                 600                 605

Val Glu Val Leu Ser Ser Thr Ser Leu Ser Leu Ala Ala Val Asn Ala
    610                 615                 620

Trp Lys Val Ala Ala Ala Glu Ser Ala Ile Ser Leu Thr Arg Gln Val
625                 630                 635                 640

Arg Glu Thr Phe Trp Ser Ala Ala Ser Thr Ser Ser Pro Ala Leu Ser
                645                 650                 655

Tyr Leu Ser Pro Arg Thr Gln Ile Leu Tyr Ala Phe Val Arg Glu Glu
            660                 665                 670

Leu Gly Val Lys Ala Arg Arg Gly Asp Val Phe Leu Gly Lys Gln Glu
        675                 680                 685

Val Thr Ile Gly Ser Asn Val Ser Lys Ile Tyr Glu Ala Ile Lys Ser
        690                 695                 700

Gly Arg Ile Asn Asn Val Leu Leu Lys Met Leu Ala
705                 710                 715

<210> SEQ ID NO 3
<211> LENGTH: 66
<212> TYPE: DNA
<213> ORGANISM: Artificial Sequence
<220> FEATURE:
<223> OTHER INFORMATION: Primer

<400> SEQUENCE: 3
aattcatcag gatctgaacg ggcagctgac ggctcgcgtg gcttaacgtc ttgagcgatt     60
gtgtag                                                               66

<210> SEQ ID NO 4
<211> LENGTH: 64
<212> TYPE: DNA
<213> ORGANISM: Artificial Sequence
<220> FEATURE:
<223> OTHER INFORMATION: Primer

<400> SEQUENCE: 4
aaaacattat ccagaacggg agtgcgcctt gagcgacacg aatatgaata tcctccttag     60
ttcc                                                                 64

<210> SEQ ID NO 5
<211> LENGTH: 40
<212> TYPE: DNA
<213> ORGANISM: Artificial Sequence
<220> FEATURE:
<223> OTHER INFORMATION: Primer

<400> SEQUENCE: 5
ctaaggagga tattcatatt cgtgtcgctc aaggcgcact                           40

<210> SEQ ID NO 6
<211> LENGTH: 66
<212> TYPE: DNA
<213> ORGANISM: Artificial Sequence
<220> FEATURE:
<223> OTHER INFORMATION: Primer

<400> SEQUENCE: 6
cgacttcatc aatttgatcg cgtaatgcgg tcaattcagc aaccatggtc tgtttcctgt     60
gtgaaa                                                               66

<210> SEQ ID NO 7
<211> LENGTH: 26
<212> TYPE: DNA
<213> ORGANISM: Artificial Sequence
<220> FEATURE:
<223> OTHER INFORMATION: Primer

<400> SEQUENCE: 7
caaccgcgca gtgaaatgaa atacgg                                         26

<210> SEQ ID NO 8
<211> LENGTH: 26
<212> TYPE: DNA
<213> ORGANISM: Artificial Sequence
<220> FEATURE:
<223> OTHER INFORMATION: Primer

```
<400> SEQUENCE: 8
gcgctccgga acataaatag gcagtc                                          26

<210> SEQ ID NO 9
<211> LENGTH: 34
<212> TYPE: DNA
<213> ORGANISM: Artificial Sequence
<220> FEATURE:
<223> OTHER INFORMATION: Primer

<400> SEQUENCE: 9
atagtagaat tcatggcacc ctcgctcgac tcga                                 34

<210> SEQ ID NO 10
<211> LENGTH: 29
<212> TYPE: DNA
<213> ORGANISM: Artificial Sequence
<220> FEATURE:
<223> OTHER INFORMATION: Primer

<400> SEQUENCE: 10
gagagactgc agagaggcag ccaagaacg                                       29

<210> SEQ ID NO 11
<211> LENGTH: 35
<212> TYPE: DNA
<213> ORGANISM: Artificial Sequence
<220> FEATURE:
<223> OTHER INFORMATION: Primer

<400> SEQUENCE: 11
ctcgctcgac tcgatctcgc actcgttcgc aaacg                                35

<210> SEQ ID NO 12
<211> LENGTH: 30
<212> TYPE: DNA
<213> ORGANISM: Artificial Sequence
<220> FEATURE:
<223> OTHER INFORMATION: Primer

<400> SEQUENCE: 12
ttgaactcga actcgatcgc gcgcaagtcg                                      30
```